United States Patent
Schwamb et al.

(10) Patent No.: US 11,974,820 B2
(45) Date of Patent: May 7, 2024

(54) SYSTEM AND METHOD FOR NAVIGATING AN INSTRUMENT

(71) Applicant: Medtronic Xomed, Inc., Jacksonville, FL (US)

(72) Inventors: Jeffrey M. Schwamb, Broomfield, CO (US); Phillip Berman, Jacksonville, FL (US); Ali Mowlai-Ashtiani, Jacksonville, FL (US); John R. Prisco, Holly Springs, GA (US); Alana M. Lacy, Chandler, AZ (US)

(73) Assignee: Medtronic Xomed, Inc., Jacksonville, FL (US)

( * ) Notice: Subject to any disclaimer, the term of this patent is extended or adjusted under 35 U.S.C. 154(b) by 13 days.

(21) Appl. No.: 17/583,301

(22) Filed: Jan. 25, 2022

(65) Prior Publication Data
US 2022/0142718 A1    May 12, 2022

Related U.S. Application Data (63) Continuation of application No. 16/055,712, filed on Aug. 6, 2018, now Pat. No. 11,241,286.

(51) Int. Cl.
*A61B 34/00* (2016.01)
*A61B 17/29* (2006.01)
(Continued)

(52) U.S. Cl.
CPC .......... *A61B 34/20* (2016.02); *A61B 17/2909* (2013.01); *A61B 34/30* (2016.02); *A61B 2017/00199* (2013.01); *A61B 2017/00389* (2013.01); *A61B 2017/00398* (2013.01); *A61B 2017/0046* (2013.01); *A61B 2017/00477* (2013.01); *A61B 2017/2901* (2013.01);
(Continued)

(58) Field of Classification Search
CPC .......... A61B 17/2909; A61B 17/32002; A61B 2017/00199; A61B 2017/00389; A61B 2017/00398; A61B 2017/0046; A61B 2017/00477; A61B 2017/2901; A61B 2017/292; A61B 2017/2948; A61B 2034/2051; A61B 2034/2055; A61B 2090/3983; A61B 34/20; A61B 34/30
See application file for complete search history.

(56) References Cited

U.S. PATENT DOCUMENTS 6,474,341 B1    11/2002    Hunter et al.
7,247,161 B2    7/2007    Johnston et al.
(Continued)

FOREIGN PATENT DOCUMENTS

WO    03013372 A2    2/2003
WO    03079911 A1    10/2003
(Continued)

OTHER PUBLICATIONS

NTAG I2C Explorer Kit user's manual, 55 pgs., 2014.
(Continued)

*Primary Examiner* — Mark D Remaly
(74) *Attorney, Agent, or Firm* — Harness, Dickey & Pierce, P.L.C.

(57) ABSTRACT

Disclosed is an instrument assembly usable in a procedure. The instrument includes a connection for a working portion and to a tool handle. A tracking device or assembly may be associated with the instrument for determining a position of the instrument.

19 Claims, 4 Drawing Sheets

(51) Int. Cl.
*A61B 34/20* (2016.01)
*A61B 34/30* (2016.01)
*A61B 17/00* (2006.01)

(52) U.S. Cl.
CPC . *A61B 2017/292* (2013.01); *A61B 2017/2948* (2013.01); *A61B 2034/2051* (2016.02); *A61B 2034/2055* (2016.02)

(56) References Cited

U.S. PATENT DOCUMENTS

| | | | |
|---|---|---|---|
| 7,697,972 | B2 | 4/2010 | Verard et al. |
| RE44,385 | E | 7/2013 | Johnson |
| 8,644,907 | B2 | 2/2014 | Hartmann et al. |
| 8,842,893 | B2 | 9/2014 | Teichman et al. |
| 9,211,163 | B1 | 12/2015 | Jaramaz et al. |
| 9,867,674 | B2 | 1/2018 | Hartmann et al. |
| 2003/0165794 | A1 | 9/2003 | Matoba |
| 2004/0199072 | A1 | 10/2004 | Sprouse et al. |
| 2013/0197552 | A1 | 8/2013 | O'Brien, II |
| 2013/0267833 | A1 | 10/2013 | Schroeder |
| 2014/0155889 | A1 | 6/2014 | Edwards et al. |
| 2014/0275980 | A1 | 9/2014 | Flores |
| 2015/0133922 | A1 | 5/2015 | Edwards et al. |
| 2015/0272608 | A1 | 10/2015 | Gladstone |
| 2016/0120609 | A1 | 5/2016 | Jacobsen et al. |
| 2016/0310218 | A1 | 10/2016 | Ruckel et al. |
| 2019/0104932 | A1 | 4/2019 | Truckai et al. |
| 2021/0275204 | A1 | 9/2021 | Gladstone |
| 2022/0142718 | A1 | 5/2022 | Schwamb et al. |

FOREIGN PATENT DOCUMENTS

| | | |
|---|---|---|
| WO | 2017/052704 A2 | 3/2017 |
| WO | 2017/163226 A1 | 9/2017 |

OTHER PUBLICATIONS

NTAG I2C Explorer Kit Contents, https://nxp-rfid.com/products/ntag/ntag-i2c-explorer-kit-contents/, 8 pgs., 2018.
International Search Report and Written Opinion regarding International Application No. PCT/US2019/045151, dated Oct. 14, 2019.
International Search Report and Written Opinion for Application No. PCT/US2019/045157, dated Nov. 22, 2019.
International Search Report and Written Opinion for Application No. PCT/US2019/045165, dated Nov. 5, 2019.
European Office Action regarding U.S. Appl. No. 19/755,485, dated Oct. 21, 2022.
U.S. Appl. No. 16/055,712, U.S. Pat. No. 11,241,286, filed Aug. 6, 201, Schwamb et al.
U.S. Appl. No. 16/055,747, 2020-0038045, filed Aug. 6, 2018, Samuel Gladstone.
U.S. Appl. No. 16/055,782, 2020-0038046, filed Aug. 6, 2018, Jeffrey M. Schwamb.
U.S. Appl. No. 17/328,164, 2021-0275204, filed May 24, 2021, Samuel Gladstone.
Examination Report for related European Application No. 19755485.0; dated Oct. 27, 2023; 4 pages.
Chinese Office Action for related Chinese Application No. 201980052099.0 dated Jan. 27, 2024.

Fig-4D

SYSTEM AND METHOD FOR NAVIGATING AN INSTRUMENT

CROSS-REFERENCE TO RELATED APPLICATIONS

This application is a continuation of U.S. application Ser. No. 16/055,712 filed on Aug. 6, 2018. This application also includes subject matter related to that disclosed in U.S. application Ser. No. 16/055,747 filed on Aug. 6, 2018, now U.S. Pat. No. 11,013,526 issued on May 25, 2021; and U.S. application Ser. No. 16/055,782 filed on Aug. 6, 2018. The entire disclosures of the above applications are incorporated herein by reference.

FIELD

Disclosed is a system for tracking an instrument, and particularly a system and method to track an instrument during a procedure with a rotating tool.

BACKGROUND

This section provides background information related to the present disclosure which is not necessarily prior art.

A surgical instrument may be used during a procedure such as within a selected region of a subject's anatomy. The surgical instrument may be out of view of a user, such as below a tissue of a subject during a procedure. A user, therefore, may be required to remove an instrument to view the exact location of the instrument or the condition of a surgical site. Accordingly, a procedure may require intermittent application of a selected surgical instrument, such as a burr.

SUMMARY

This section provides a general summary of the disclosure, and is not a comprehensive disclosure of its full scope or all of its features.

A driver may power an instrument, such as a burr or other resection or driven instrument during a selected procedure. The instrument may be removably connected to a driver, such as a powered tool handle. The powered tool handle may include a motor and a portion that is graspable by a user, such as surgeon.

In using the instrument during the procedure, the user may desire or select to navigate the instrument. In navigating the instrument, a tracked location of at least a portion of the instrument is determined. In tracking the instrument, a navigation system may determine and illustrate a position of the instrument relative to an image of the subject or patient for a selected period of time.

The tracking device may include selected portions that are interconnected or formed with the instrument. The instrument may include a working end, an elongated shaft, and a hub or connection portion to connect to the tool handle. The hub portion may incorporate various portions, such as the tracking device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
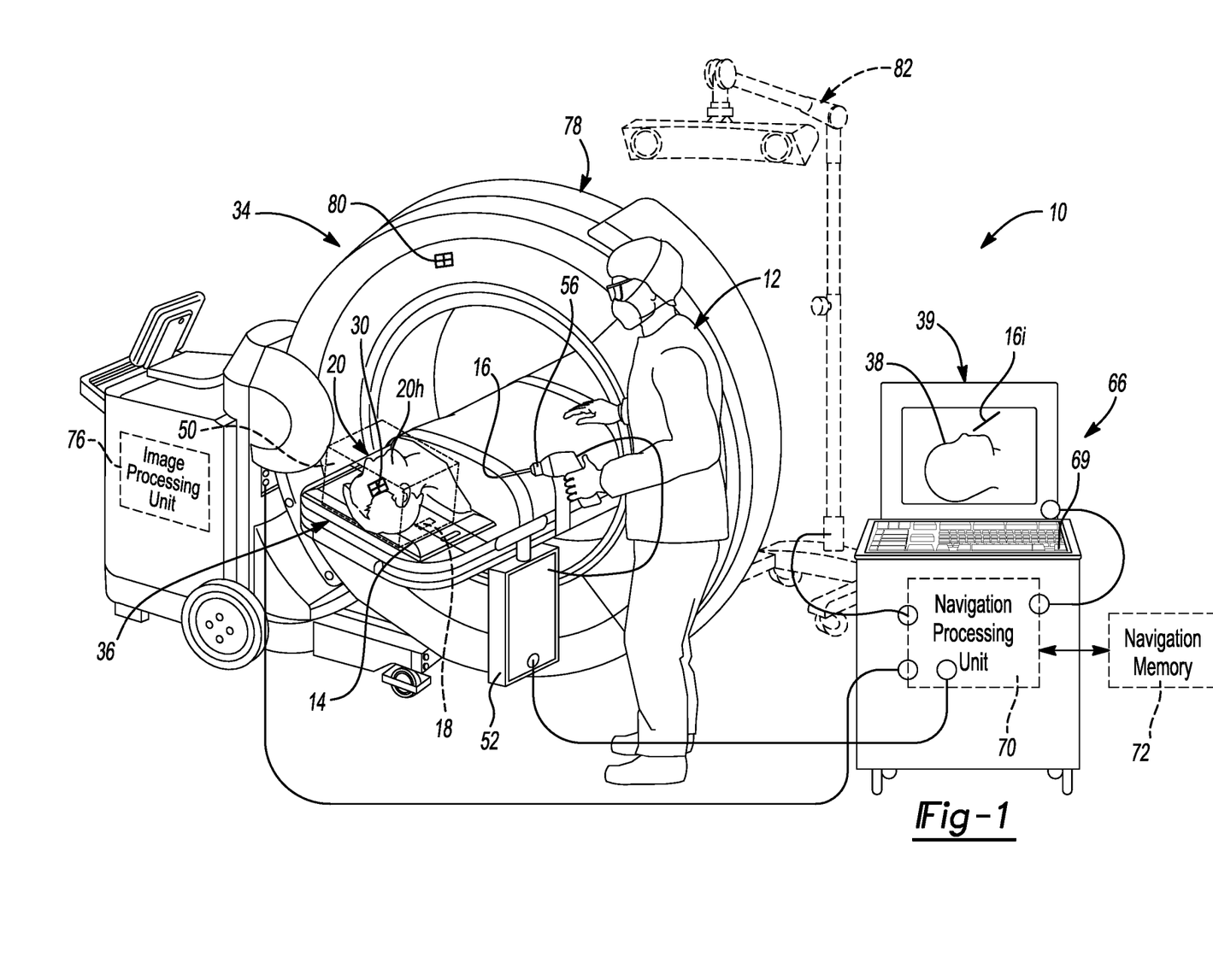
FIG. 1 is an environmental view of an operating theater with a tracking system.

With initial reference to FIG. 1, in a procedure a navigation system 10 may be used by a user 12 to perform a selected procedure. The navigation system 10 may include various components that assist in navigating a procedure including a selected tracking system. The tracking system may include various components or portions such as various localizers. Various localizers may include an optical tracking system and/or an electromagnetic tracking system that includes a Tracking Coil Array (TCA) localizer 14. While the optical tracking system may be used in conjunction with or simultaneously with the TCA 14, it is understood that only one tracking system may be used with the navigation system 10. In various embodiments, therefore, both an optical localizer 82 and the TCA 14 may be used together or simultaneously for tracking one or more instrument, or only one. An instrument 16 may be tracked during a selected procedure, such as a navigated procedure with the navigation system 10.

The TCA 14 may include one or more conductive coils 18 positioned relative to a subject 20 on which a procedure is performed. In various embodiments, a procedure may be performed on or near a head 20h of the subject 20. As discussed in further detail herein, a subject tracking device or assembly 30 may be connected to the subject 20, such as to the head 20h of the subject 20. The tracking assembly 30 may also be referred to as a Dynamic Reference Frame (DRF) or a patient tracker.

With continuing reference to FIG. 1, the navigation system 10 may include various features or elements as discussed below. Generally, the navigation system 10 may be used to determine or track a position of an instrument 16 in a volume. The position may include both a three dimensional X,Y,Z location and orientation. Orientation may include one or more degrees of freedom, such as three degrees of freedom. Thus, a total of at least six degrees of freedom may be determined for the position of the instrument 16.

Tracking the position of the instrument 16 may assist the user 12 in determining a position of the instrument 16, even if the instrument 16 is not directly viewable by the user 12. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 20 and the procedure may be performed on the human subject 20. It is understood, however, that the instrument 16 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 10, as discussed further herein, may incorporate various portions or systems, such as those disclosed in U.S. Pat. Nos. RE44,385; 7,697,972; 8,644,907; and 8,842,893; and U.S. Pat. App. Pub. Nos. 2004/0199072, all incorporated herein by reference. Various components that may be used with or as a component of the surgical navigation system 10 may include an imaging system 34 that is operable to image the subject 20, such as an O-arm® imaging system, magnetic resonance imaging (MRI) system, computed tomography system, etc. A subject support 36 may be used to support or hold the subject 20 during imaging and/or during a procedure. The same or different supports may be used for different portions of a procedure.

Image data may be acquired during a surgical procedure or acquired prior to a surgical procedure for displaying an image 38 on a display device 39. The instrument 16 may be tracked in a trackable volume or a navigational volume that is produced by the transmitter antenna or transmitting coil array 18 that is incorporated into the localizer 14, as illustrated in FIG. 1. The position of the instrument 16 may be tracked in the tracking volume relative to the subject 20 and then illustrated as an icon 16i with the display device 39. In various embodiments, the icon 16i may be superimposed on the image 38 and/or adjacent to the image 38. As discussed herein, the navigation system 10 may incorporate the display device 39 and operate to render and display the image 38, from image data. Also, the determined the position of the instrument 16 may be performed and displayed with the display device 39, such as the icon 16i.

With reference to FIG. 1, the localizer 14 may be an electro-magnetic (EM) localizer that is operable to generate electro-magnetic fields with coils 18 of the transmitting coil array (TCA) 14 which is incorporated into the localizer 14. The TCA 14 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 18 and form a navigation domain or volume 50, such as encompassing all or a portion of a head 20h, spinal vertebrae, or other appropriate portion. The coils 18 may be powered through a TCA controller and/or power supply 52.

The navigation domain or volume 50 generally defines a navigation space or patient space. As is generally understood in the art, the instrument 16, such as a drill, lead, etc., may be tracked in the navigation domain relative to a patient or subject with an instrument tracking device 56. For example, the instrument 16 may be freely moveable, such as by the user 12, relative to the DRF 30 that is fixed relative to the subject 20. Both the tracking devices 30, 56 may include tracking or sensing coils (e.g. conductive material formed or placed in a coil) that senses and are used to measure a magnetic field strength, etc. Due to the tracking device 56 connected or associated with the instrument 16, relative to the DRF 30, the navigation system 10 may be used to determine the position of the instrument 16 relative to the DRF 30.

The navigation volume or patient space may be registered to an image space of the patient and the icon 16i representing the instrument 16 may be illustrated at a navigated (e.g. determined) and tracked position with the display device 39, such as superimposed on the image 38. Registration of the patient space to the image space and determining a position of a tracking device, such as with the tracking device 56, relative to a DRF, such as the DRF 30 may be performed as generally known in the art, including as disclosed in U.S. Pat. Nos. RE44,385; 7,697,972; 8,644,907; and 8,842,893; and U.S. Pat. App. Pub. Nos. 2004/0199072, all incorporated herein by reference.

The navigation system 10 may further include a navigation processor system 66. The navigation processor system 66 may include the display device 39, the localizer 14, the TCA controller 52, and other portions and/or connections thereto. For example, a wire connection may be provided between the TCA controller 52 and a navigation processing unit 70. Further, the navigation processor system 66 may have one or more user control inputs, such as a keyboard 69, and/or have additional inputs such as from communication with one or more memory systems 72, either integrated or via a communication system. The navigation processor system 66, according to various embodiments, may include those disclosed in U.S. Pat. Nos. RE44,385; 7,697,972; 8,644,907; and 8,842,893; and U.S. Pat. App. Pub. Nos. 2004/0199072, all incorporated herein by reference, and/or may also include the commercially available StealthStation® or Fusion™ surgical navigation systems sold by Medtronic Navigation, Inc. having a place of business in Louisville, CO.

Tracking information, including regarding the magnetic fields sensed with the tracking devices 30, 56, may be delivered via a communication system, such as the TCA controller 52, which also may be a tracking device controller 52, to the navigation processor system 66 including the navigation processor 70. Thus, the tracked position of the instrument 16 may be illustrated as the icon 16i relative to the image 38. Various other memory and processing systems may also be provided with and/or in communication with the processor system 66, including the memory system 72 that is in communication with the navigation processor 70 and/or an imaging processing unit 76. The image processing unit 76 may be incorporated into the imaging system 34, such as the O-arm® imaging system, as discussed above. The imaging system 34 may, therefore, include various portions such as a source and a x-ray detector that are moveable within a gantry 78. The imaging system 34 may also be tracked with a tracking device 80. It is understood, however, that the imaging system 34 need not be present while tracking the tracking devices, including the instrument tracking device 56. Also, the imaging system 34 may be any appropriate imaging system including a MRI, CT, etc. In various embodiments, the localizer may also include an optical camera system 82. The optical camera system 82 may be used in conjunction with or alternatively to the localizer 14 for tracking the instrument 16.

Information from all of the tracking devices may be communicated to the navigation processor 70 for determining a position of the tracked portions relative to each other and/or for localizing the instrument 16 relative to the image 38. The imaging system 34 may be used to acquire image data to generate or produce the image 38 of the subject 20. It is understood, however, that other appropriate imaging systems may also be used. The TCA controller 52 may be used to operate and power the TCA 14, as discussed above.

With continuing reference to FIG. 1 and additional reference to FIGS. 2-4D, the instrument 16 may include various portions such as a distal or working end 100. The working end 100 may be formed as a selected instrument working end or portion, such as a burr, grinder, cutter, or cutting tool that is rotated by a motor 104 within a handle or tool handle 106. The tool handle 106 may be held with a single hand of the user 12 and be operated by the user 12. In various embodiments, a foot switch is provided to power on and off the motor 104 while the user holds the handle 106. The instrument 16 may further include an elongated tube or shaft 110. The elongated tube 110 may include an internal and/or external portion, such as the tools sold with the StraightShot® M5 power handle, by Medtronic, Inc., having a place of business in Minneapolis, Minnesota. In various embodiments, the shaft 110, may be included as an elongated tube or a tubular shaft.

Figure 2:
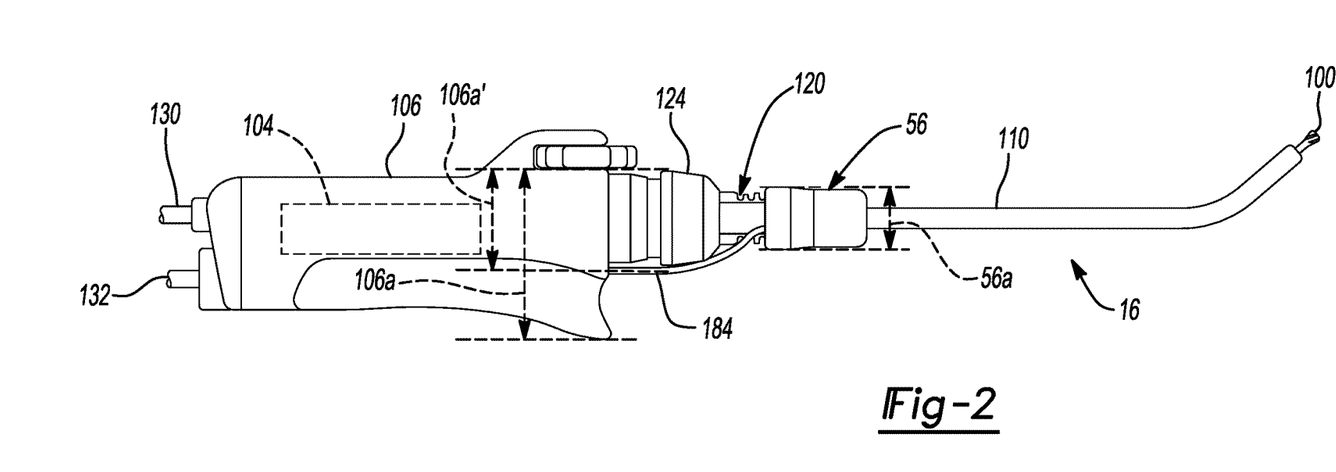
FIG. 2 is a perspective view of a tool and instrument, according to various embodiments.

The instrument 16, including the elongated tube 110, may include an exterior wall having an interior cannula through which the working end 100 is powered, such as by an elongated shaft 101 to drive the working end 100. As discussed further herein, the shaft 101 driving the working end 100 may connect with the motor 104 through a hub 120. The hub 120 may engage a collet 124 to hold or fix the instrument 16 relative to the handle 106.

In various embodiments, irrigation may be provided through the instrument 16, such as through or by an irrigation barb 226. It is understood that the irrigation barb 226 may be connected with an irrigation hose or tubing to provide irrigation through the instrument 16. Further, suction may be drawn or pulled through the instrument 16, and through the handle 106, such as through a suction tube 130. The suction tube 130 and an electrical connection line 132 may be connected to a console or controller, which may be incorporated with the TCA controller 52. It is understood that the console or controller may be similar to the console Medtronic IPC® power and control console or System, sold by Medtronic, Inc. Nevertheless the instrument 16 may be moved and powered by the handle 106 when operated by the user 12.

Figure 3:
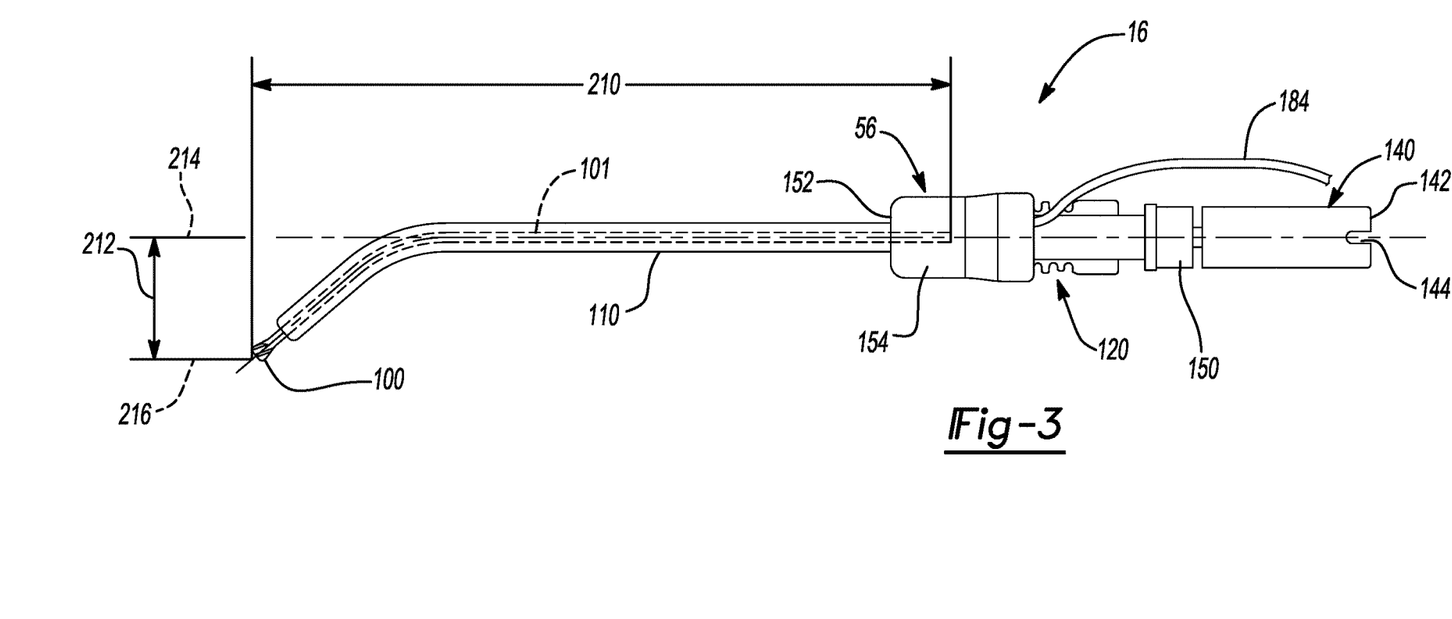
FIG. 3 is a detailed view of an instrument with a tracking device, according to various embodiments.

In various embodiments, the tracking device 56 may be incorporated into or onto the hub 120. With exemplary reference to FIG. 3-4C, the tracking device 56 may be incorporated onto the hub 120 of the instrument 16. The hub 120 of the instrument 16, as illustrated in FIG. 3, may be connected to the shaft 110 through which the shaft 101 of the bit or working end 100 passes. The shaft 101 extends through the hub 120 and may terminate and/or engage a tongue 140. The tongue 140 may terminate and/or have a terminal end 142. The terminal end 142 may have a keyed or engaging portion, such as an engaging wall 144 to engage an internal element in the handle 106. For example, a shaft extending from the motor 104 may engage the engaging wall 144 of the tongue 140. An interference between the shaft extending from the motor 104 and the engaging wall 144 may allow for transfer of forces from the motor 104 to the tongue 140. As the tongue 140 is connected to the bit shaft 101, the working end 100 may then rotate due to a force transferred through the tongue 140. The shaft 101, passing through the hub 120, may allow for the hub 120 to be positioned or moveable relative to the handle 106 and carry various components, such as the tracking device 56 relative thereto.

Generally, the bit shaft 101, working end 100, tongue 140, and hub 120 components are provided as a single assembly, such as from a supplier. Thus, the user 12 may connected the instrument 16 to the handle 106, including the motor 104, as a single action or assembly. Further, the instrument may be a single use or one time use instrument. This allows the instrument to be useable with the handle 106 for the procedure, including tracking of the instrument 16, while allowing ease or assembly and efficient sterile preparation and disposal.

Figure 4A:
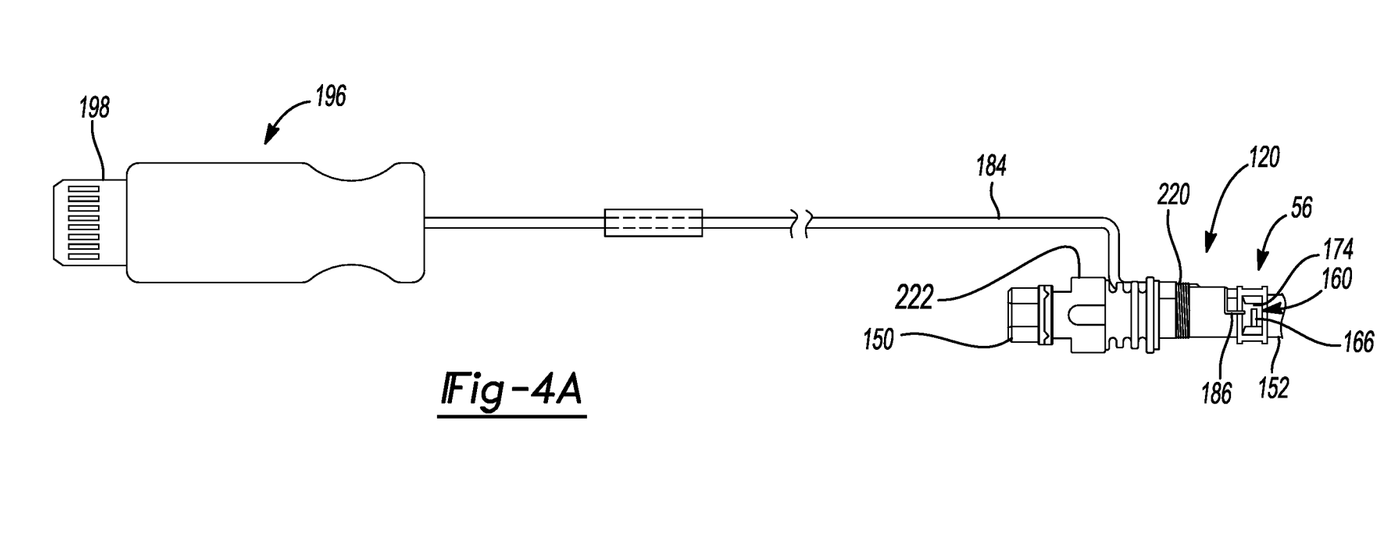
FIGS. 4A-4C are different plan views of an instrument hub and connector rotated around a long axis of the hub, according to various embodiments.
Figure 4B:
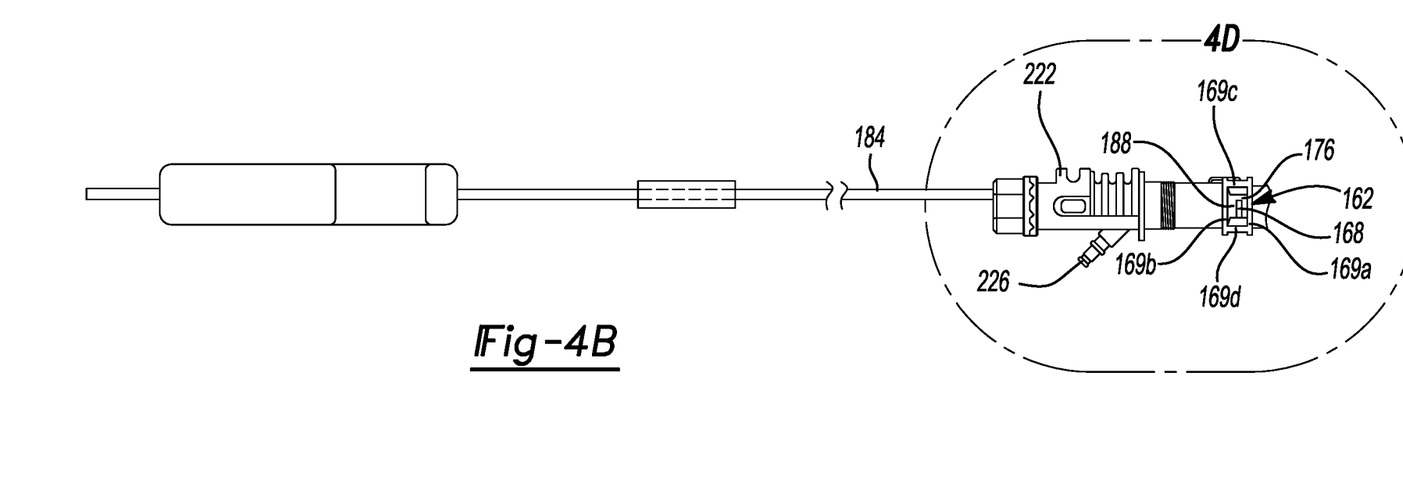
Figure 4C:
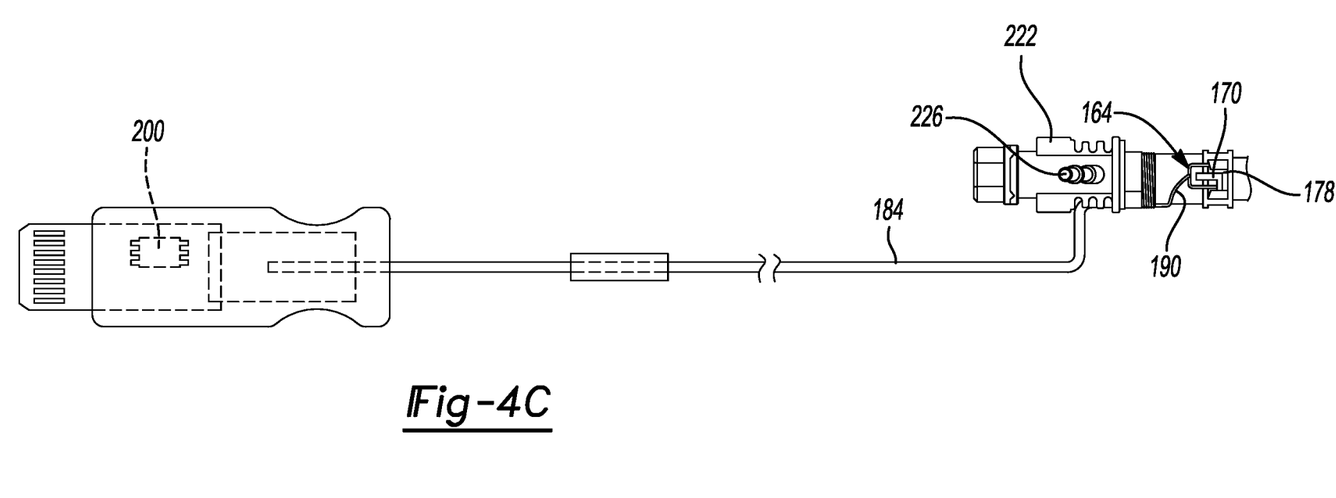
Figure 4D:
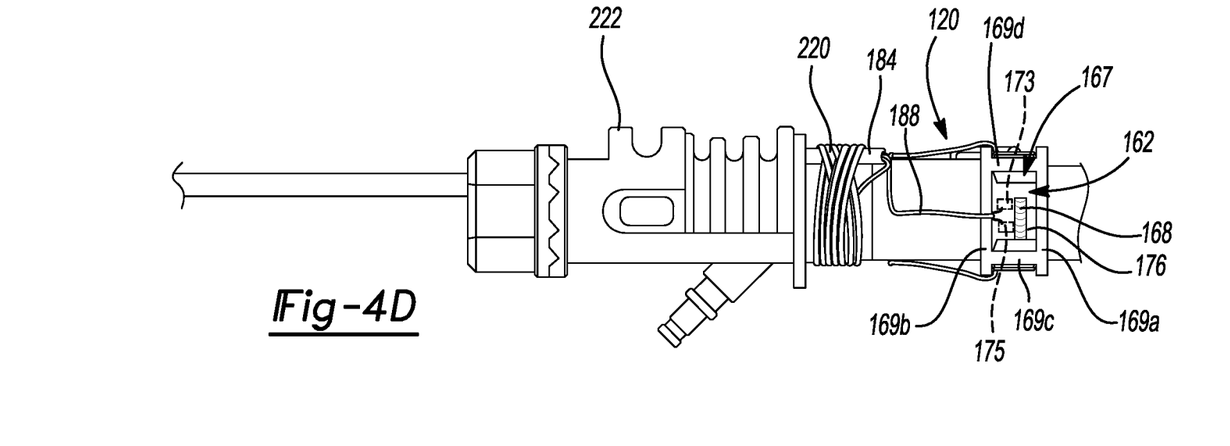
FIG. 4D is a detail view of a hub.

The hub 120 is illustrated in greater detail in FIGS. 4A, 4B, and 4C and discussed below. A detail view of the hub 120 is illustrated in FIG. 4D. Initially, the working end 100 and the associated shaft 101 may be formed of a selected material, such as a metal or metal alloy. In various embodiments, the shaft 110 of the instrument 16 may also be formed of a selected metal or metal alloy material. The hub 120 may be formed as a single member either with the shaft 110 or separate therefrom. For example, the hub 120 may be formed of a selected polymer material that may be over molded or injection molded onto the shaft 110. It is understood, however, that the hub 120 may be formed separately from the shaft 110 and connected during assembly of the instrument 16. Moreover, it is understood that the hub 120 may be formed of selected appropriate materials such as polymers, co-polymers, metal alloys, selected bearing materials, combinations thereof, or the like.

The hub 120 generally extends from a proximal end 150 to a distal end 152. The proximal end 150 and distal end 152 may further be terminal ends of the hub 120. As illustrated in FIG. 3, and discussed further herein, at least a portion of a distal portion, such as extending from the distal end 152 toward the proximal end 150, may be a covering or encapsulation 154. The encapsulation portion or member 154 may include a wrapping or shrink wrap formed over selected portions of the hub 120, as discussed further herein. It is further understood that the cover 154 may a rigid member that is passed on to the hub 120, such as over the shaft 110. The tracking device 56, even when covered, may have an external dimension (e.g. cross-sectional diameter) 56a that is less than or equal to an external dimension 106a of a portion of the handle near or adjacent to the hub 120 and/or external dimension 106a' of a chuck or instrument attachment. Thus, the hub 120 including the tracking device 56 may allow a large field of view and efficient operation of the instrument 16 and the handle 106.

For example, positioned on and/or fixed to the hub 120 may be a plurality of tracking elements or members that form the tracking device 56. The tracking elements may include a first tracking coil assembly 160, a second tracking coil assembly 162, and a third tracking member 164. Each of the tracking members 160, 162, 164 may incorporate or form a portion of the tracking device 56. For example, each of the member portions 160, 162, 164 may include a coil, such as a micro coil 166, 168, 170, respectively. The coils 166-170 may be formed around an inner core or a magnetically permeable core and positioned relative to a contact member or support. The coils 166-170 may be formed of a selected wire or connective material of a selected diameter. For example, the coils are formed by winding around an air core or selected core and in selected ends. Each of the coils 166-170 may be placed or connected to a board, such as a printed circuit board 174, 176, 178, respectively. The ends of the coils 166-170 may be mounted or fixed to selected conductive portions of the respective boards 174-178.

With reference to FIG. 4D, the coil assembly 162 is illustrated in greater detail. The hub 120 may include various mounting or fitting portions. For example, a well or holding region 167 may be defined by walls. An end wall 169a, a proximal wall 169b, and one or more side walls 169c, 169d may extend from a surface of the hub 120. The walls 169 may form or define the well to receive or hold the coil assembly 162 in a selected position, including location and orientation relative to the hub 120. The well may assist in manufacturing such as that the coil assembly 162 is positioned in a selected and appropriate position for each hub 120. Further, each of the coil assemblies may be placed in similar wells.

The coil 168 may include ends of the coiled wire that are mounted to the board 176, such as to pads. The board 176 may include traces to additional pads 173, 175. The pads 173, 175 on the board 176 allow for a connection, such as an efficient and repeatable connection, of the connector 188. Again, one skilled in the art will understand that each coil assembly may include a similar assembly.

The coil and board assemblies may then be fixed to the hub 120 in a selected manner. For example, the coils may be respectively epoxied or adhered to the respective boards 174-178. The epoxied assemblies may be adhered or epoxied to the hub 120, such as into the well or pockets 167. Generally, the member portions 160, 162, 164 generally have similar or identical dimensions and a generally rectangular shape having dimensions of about 2 millimeters (mm) to about 6 millimeters per side, where measurements may include a measurement and/or manufacturing tolerance of about 0.01 mm to about 2 mm. Exemplary dimensions may include about 5 mm by about 3 mm, about 3 mm by about 2 mm, about 3.05 mm by 3.81 mm, and about 2.54 mm by about 5.33 mm. Generally, the member portions may have an area of about 13 $mm^2$, including less than about 20 $mm^2$, less than about 15 $mm^2$ and about less than about 8 $mm^2$.

Further, a connector or communication line 184 may have selected twisted pair wires leads for each of the boards, such as a first lead 186, a second lead 188, and a third lead 190. Each of the respective leads 186-190 may also be fixed to the respective boards 174-178. It is understood that the respective leads 186-190 and the terminal ends of the coils 166-170 may be soldered or selectively affixed to the respective boards 174-178, as is generally understood in the art.

The leads may pass along the common connector line 184 to a proximal connector 196. The connector 196 may include a physical connection 198 to a selected console or assembly, such as the TCA controller 52. As discussed herein navigation or tracking information from the tracking device 56 may be transmitted along the common connector 184 to the connector 196 and the physical connection 198.

In the connector 196, in various embodiments, the physical connector 198 may include a selected memory and/or processor assembly 200. The memory and/or processor assembly 200 may include information regarding the instrument 16 to which the hub 120 is affixed. Information may include a geometry, such as a geometric position of the working end relative to the tracking device. For example, the information may include a distance 210, along an axis 214 of the instrument 16, from the tracking device may be the information. In addition and/or alternatively thereto, the information may include an offset distance 212 from the axis 214 of the instrument 16 to a working terminal end plane or position 216 of the working end 100.

Accordingly, the memory and/or processor assembly 200 may have calibrated a predetermined or known positions of the working end 100 relative to the tracking device 56 stored thereon. The stored information may be transferred to the navigation system 10 when the physical plug 198 has attached to the TCA controller 52. In transmitting the information, such as with a signal from the memory and/or processor assembly 200 to the navigation processor system 66, the processor system 66 is able to access or determine the calibrated position of the working end 100 relative to the tracking device 56.

The hub 120 may further include other components such as a fixation portion or member 220 to assist in holding the single line 184 relative to the hub 120. The fixation 220 may be a selected adhesive, wrapping, insulation wrapping, or the like. Further the hub 120 may include selected connection features, such as keyed or non-cylindrical features 222 which may include interference walls or facets. Further, the hub 120 may include an irrigation line connection, such as hose barb 226 to allow for a connection of an irrigation line to the hub 120. In various embodiments, the irrigation line may be connected to the barb 226 to provide a delivery of fluid through the hub 120 and thereafter through the shaft 110 around the working end 100. A suction may also be provided through a second inner cannula due to the suction line 130, as discussed above.

To assist in tracking the instrument 16, or portions thereof, the tracking device 56 includes the tracking members 160, 162, 164 that are selectively positioned on the hub 120. For example, each of the respective coils 166-170 may be positioned at about 100 to about 150 degrees, including about 120 or exactly 120 degrees, around the axis 214 relative to one another. It is understood that the tracking members 160-164 may be selectively positioned for various purposes.

Each of the respective coils 166-170 may be orthogonally positioned relative to one another. The field generated by the TCA 14 may then be sensed by the coils 166-170 positioned on the hub 120. That is the first coil 166 may sense a field that has a main axis that is substantially perpendicular to field sensed by the second coil 166 and the third coil 170. To sense the field in the selected orientations, the respective coils 166-170 may be positioned on the respective boards 174-178 in a selected manner or each of them may be formed connectively and positioned at different orientations on the hub 120. It is understood, by one skilled in the art, that the coils 166-170 may also generate respective fields (e.g. orthogonal to one another) that are sensed by the TCA 14 for tracking of the tracking device 56.

During use of the navigation system 10, such as when the user 12 is moving an instrument 16 relative to the subject 20, the tracking device 56 may sense the field generated by the TCA 14. As discussed above the sensed field may be used to determine a position of the instrument 16, such as a position of the working end 100, relative to the subject 20. In various embodiments, the DRF 30 may be used in combination with the tracking device 56 to determine the relative positon of the instrument 16 relative to the subject 20. Accordingly, as discussed above, the icon 16i may be illustrated on the display device 39 to illustrate the position of the instrument 16 relative to the subject 20.

In having the tracking members 160-164 positioned at the respective locations on the hub 120, such as orientated orthogonally to one another, a selected degrees of freedom may be determined regarding the position of the tracking device 56. For example, six degrees of freedom may be determined including a three dimensional (e.g. x,y,z location) and orientation (e.g. three degrees of freedom). It is understood, however, that less than three of the tracking members may be used with the tracking device 56. Thus, as the motor 104 powers (e.g. rotates) the shaft 101 of the instrument 16, the position of the working end 100 may be determined and illustrated as the icon 16*i*. During operation of the instrument 16 (e.g. rotating and resecting) and moving the instrument 16 (e.g. toward and away from a surface) tracking of the tracking device 56 occurs.

Further, the dimension or position of the working end 100 relative to the tracking device 56 may be recalibrated or determined during a procedure. For example, the user 12 may position the working end 100 relative to the DRF 30 at a selected or known position. The navigation system 10 may then calibrate or determine the position of the working end 100 relative to the tracking device 56 by determining or tracking the DRF 30 and the tracking device 56. The instrument 16 may then be connected to the handle 106, if not already connected, and the navigation may proceed without a predetermined calibration or pre-known position of the working end 100 relative to the tracking device 56.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for determining a position of a working end of a driven instrument, comprising:
    an elongated tubular member having a cannula therein;
    a hub connected to the elongated tubular member; and
    a tracking device having a plurality of tracking members connected to the hub;
    wherein the hub is configured to be connected to a tool motor handle having a tool motor to drive a shaft;
    wherein the hub defines a plurality of recessed wells formed into the hub and each recessed well houses at least one of the plurality of tracking members within each recessed well.

2. The system of claim 1, further comprising:
    the shaft positioned and extending through the cannula; and
    the working end attached to the shaft and extending from the elongated tubular member to be driven by the shaft.

3. The system of claim 2, wherein the shaft extends through the hub.

4. The system of claim 3, further comprising:
    the tool motor handle;
    wherein the elongated tubular member, the hub, the tracking device, the shaft, and the working end are configured as an assembly and attached to the tool motor handle as a single unit.

5. The system of claim 1, wherein each recessed well includes a plurality of walls to form a plurality of rectangular-shaped wells.

6. The system of claim 1, wherein each tracking member includes a coil of conductive material formed around a core and a printed circuit board;
    wherein the conductive material is connected to the printed circuit board and positioned with a well.

7. The system of claim 2, wherein the working end includes a burr, a rotating cutter, a grinder, or combinations thereof.

8. The system of claim 1, further comprising:
    a connector electrically connected to the tracking device;
    wherein the connector includes a memory having calibration information regarding the drive instrument.

9. The system of claim 1, wherein the plurality of tracking members includes three tracking members positioned radially about the hub.

10. A system for determining a position of a working end of a driven instrument, comprising:
    an instrument assembly, including:
        an elongated tubular member having a cannula therein;
        a working tool having a shaft extending through the cannula and a working end attached to the shaft, wherein the working end extends from the elongated tubular member and configured to be driven by the shaft;
        a hub fixedly connected to the elongated tubular member, wherein the shaft extends through the hub, the hub defines a recessed well within the hub; and
        a tracking device connected to the hub, wherein the tracking device includes at least one tracking member positioned within the recessed well having a dimension less than about 20 square millimeters; and
    a tracking system configured to track a position of the tracking device;
    wherein the hub is configured to be connected to a tool motor to drive the shaft.

11. The system of claim 10, further comprising:
    the tool motor having a handle and a motor;
    wherein the working tool is rotated by the motor while the tracking system tracks the tracking device.

12. The system of claim 11, wherein an external dimension of the hub and tracking device is less than a dimension of the handle adjacent to the hub.

13. The system of claim 10, wherein the hub includes a wall having an external surface and the tracking device is adhered to the external surface of the hub.

14. The system of claim 13, wherein the hub includes a plurality of recessed well forming walls extending from the external surface;
    wherein the tracking device is adhered to the external surface of the hub within a recessed well defined by the plurality of recessed well forming walls.

15. A system to track an instrument, comprising:
    a hub extending along an axis;
    a tubular member connected to the hub;
    a tracking member affixed within a rectangular-shaped well defined by the hub;
    wherein the hub is configured to be fixed to a power tool handle.

16. The system of claim 15, wherein the tracking member is configured to track a position of a working end connected to an instrument shaft while the instrument shaft rotates.

17. The system of claim 16, wherein the tracking member is affixed to the well and defines an external dimension less than an external dimension of the power tool handle.

18. The system of claim 15, further comprising:
the power tool handle, wherein the power tool handle includes a motor configured to selectively rotate an instrument shaft.

19. The system of claim 18, wherein the power tool handle is operable to be manipulated by a single hand of a user to perform a procedure.

* * * * *

UNITED STATES PATENT AND TRADEMARK OFFICE
CERTIFICATE OF CORRECTION

| | | |
|---|---|---|
| PATENT NO. | : 11,974,820 B2 | Page 1 of 1 |
| APPLICATION NO. | : 17/583301 | |
| DATED | : May 7, 2024 | |
| INVENTOR(S) | : Jeffrey M. Schwamb et al. | |

It is certified that error appears in the above-identified patent and that said Letters Patent is hereby corrected as shown below:

On the Title Page

Page 2, Column 2, item (56) Other Publications, Lines 11-12, Delete "Aug. 6, 201," and insert --Aug. 6, 2018,-- therefor In the Specification Column 8, Detailed Description, Line 53, Delete "positon" and insert --position-- therefor Signed and Sealed this
Fourth Day of March, 2025

Coke Morgan Stewart
*Acting Director of the United States Patent and Trademark Office*